US011288848B2

(12) United States Patent
Zheng et al.

(10) Patent No.: US 11,288,848 B2
(45) Date of Patent: Mar. 29, 2022

(54) THREE-DIMENSIONAL ULTRASOUND IMAGE DISPLAY METHOD (71) Applicant: Telefield Medical Imaging Limited, Hong Kong (HK)

(72) Inventors: Yongping Zheng, Hong Kong (HK); Qiang Meng, Hong Kong (HK)

(73) Assignee: Telefield Medical Imaging Limited, Hong Kong (HK)

( * ) Notice: Subject to any disclaimer, the term of this patent is extended or adjusted under 35 U.S.C. 154(b) by 237 days.

(21) Appl. No.: 16/629,586

(22) PCT Filed: Jul. 3, 2018

(86) PCT No.: PCT/CN2018/094311
§ 371 (c)(1),
(2) Date: Jan. 9, 2020

(87) PCT Pub. No.: WO2019/011160
PCT Pub. Date: Jan. 17, 2019

(65) Prior Publication Data
US 2021/0110580 A1  Apr. 15, 2021

(30) Foreign Application Priority Data

Jul. 11, 2017 (CN) .......................... 201710559995.9

(51) Int. Cl.
*A61B 8/00* (2006.01)
*G06K 9/00* (2022.01)
(Continued)

(52) U.S. Cl.
CPC .......... *G06T 11/005* (2013.01); *A61B 8/0875* (2013.01); *A61B 8/14* (2013.01);
(Continued)

(58) Field of Classification Search
USPC ........ 382/100, 103, 106, 128–132, 154–156, 382/166, 168, 173, 181, 189, 199, 219,
(Continued)

(56) References Cited

U.S. PATENT DOCUMENTS

2011/0021914 A1* 1/2011 Zheng ................... A61B 5/103
600/443
2013/0331697 A1* 12/2013 Park ...................... A61B 8/466
600/440

(Continued)

FOREIGN PATENT DOCUMENTS

EP          2682060 A1    1/2014

OTHER PUBLICATIONS

International Search Report of PCT Patent Application No. PCT/CN2018/094311 dated Sep. 26, 2018.

*Primary Examiner* — Seyed H Azarian (57) ABSTRACT

Disclosed is a three-dimensional ultrasound image display method comprising the following steps: S1: obtaining a series of original two-dimensional images having spatial position and angle information by means of automatic or manual scanning; S2: performing image reconstruction on the basis of the original two-dimensional images to obtain three-dimensional volumetric images; S3: obtaining, from the three-dimensional volumetric images, one or more section images intersecting the original two-dimensional images, and obtaining one or more reconstructed two-dimensional images by means of image processing; S4: displaying together the one or more original two-dimensional images and the one or more section images in a three-dimensional space; and S5: selecting and displaying feature points, feature lines, and feature surfaces in the three-dimensional space on the basis of the original two-dimensional volumetric images. The present method provides an efficient and high-precision three-dimensional (Continued)

image display method, which can be widely applied to ultrasound and other three-dimensional imaging modes.

13 Claims, 8 Drawing Sheets

(51) Int. Cl.
  *G06T 11/00* (2006.01)
  *A61B 8/08* (2006.01)
  *A61B 8/14* (2006.01)
  *G06T 5/00* (2006.01)
  *G06T 7/00* (2017.01)

(52) U.S. Cl.
  CPC ............ *A61B 8/4461* (2013.01); *A61B 8/463* (2013.01); *A61B 8/466* (2013.01); *A61B 8/469* (2013.01); *G06T 5/001* (2013.01); *G06T 7/0012* (2013.01); *G06T 11/001* (2013.01); *A61B 2503/06* (2013.01); *G06T 2207/10136* (2013.01); *G06T 2207/30012* (2013.01); *G06T 2210/41* (2013.01)

(58) Field of Classification Search
  USPC .... 382/232, 254, 276, 285–291, 305; 378/4, 378/21; 600/301, 440, 443, 437
  See application file for complete search history.

(56) References Cited

U.S. PATENT DOCUMENTS

| | | | |
|---|---|---|---|
| 2015/0173668 A1* | 6/2015 | Zheng | A61B 5/4561 600/301 |
| 2017/0020626 A1* | 1/2017 | Schlenger | A61B 5/4566 |
| 2020/0273169 A1* | 8/2020 | Mauldin | A61B 8/5269 |
| 2021/0137490 A1* | 5/2021 | Zheng | A61B 8/0875 |

* cited by examiner

THREE-DIMENSIONAL ULTRASOUND IMAGE DISPLAY METHOD

TECHNICAL FIELD

The present disclosure relates generally to the ultrasound imaging technical field, and more particularly relates to a three-dimensional ultrasound image display method.

BACKGROUND

Scoliosis is a medical condition in which the patient's spine bends from one side to the other side and may also rotate. X-ray evaluation is usually used to determine the scoliosis. During the treatment or monitoring process, many radiographs of the patients with scoliosis must be obtained, which results in high dose of radiation exposure on the. Accordingly, such technology is not suitable for children and adolescents patients.

In recent years, three-dimensional ultrasound imaging technology has been widely used in the medicine and medical research. Most of the three-dimensional ultrasound imaging systems acquire a series of two-dimensional images (B-ultrasound images) with spatial position and angle information, with scanning being conducted manually or automatically for realizing the three-dimensional ultrasound image. For example, the three-dimensional ultrasound system used in fetus observation is realized by the mechanical scanning, while the three-dimensional ultrasound imaging system of spine is usually realized by the manual scanning.

At present, there are two ways to display the series of two-dimensional ultrasound images with spatial position and angle information. The first way is to directly display the corresponding two-dimensional ultrasound images with spatial position and angle in the three-dimensional space, by displaying one or more images simultaneously. However, this method cannot provide information of the other section images. The second way is to reconstruct the two-dimensional image by using the corresponding spatial position information of all the two-dimensional ultrasound images. During the reconstruction process, some parts which are not scanned by the two-dimensional imaging process will be interpolated, but meanwhile some smoothing processes would be performed on the image. Accordingly, the quality of the formed image is not as good as the original two-dimensional image, and after the image processing, and some original information will be lost.

SUMMARY

The objective of the present application is to provide a three-dimensional ultrasound image display method which is capable of displaying and analyzing three-dimensional volumetric images conveniently while maintaining the original image quality, aiming at the above problems of the prior art.

In one aspect, a three-dimensional ultrasound image display method is provided for solving above technical problem, which including following steps:

S1. obtaining a series of original two-dimensional images having spatial position and angle information by means of automatic or manual scanning;

S2. performing an image reconstruction based on the original two-dimensional image to obtain a three-dimensional volumetric image;

S3. obtaining, from the three-dimensional volumetric image, one or more section images intersecting the original two-dimensional image, and obtaining one or more reconstructed two-dimensional images by means of image processing;

S4. displaying together the one or more original two-dimensional images and the one or more section images in a three-dimensional space; and S5. selecting and displaying a feature point, a feature line, and a feature surface in the three-dimensional space based on the original two-dimensional image.

Advantageously, the three-dimensional ultrasound image display method further comprises implementing an image enhancement or pseudo color rendering on the original two-dimensional image, reconstructed two-dimensional image and section image for enhancing details displayed in the original two-dimensional image and the reconstructed two-dimensional image.

Advantageously, in step S5, a step of selecting and displaying a feature point, a feature line, and a feature surface further comprises following steps:

S5-1. marking information of the feature point, the feature line or the feature surface on one of the original two-dimensional image, the section image or the reconstructed two-dimensional image;

S5-2. automatically displaying the information of the feature point, the feature line or the feature surface determined in S5-1 on the original two-dimensional image, the section image or the reconstructed two-dimensional image;

S5-3. determining whether the information of the feature point, the feature line or the feature surface marked in the original two-dimensional image, the section image or the reconstructed two-dimensional image is accurate or not;

S5-4. adjusting inaccurate marked information determined in S5-3 accordingly;

S5-5. repeating steps S5-2 to S5-4 until the information of the feature point, the feature line or the feature surface marked in the original two-dimensional image, the section image or the reconstructed two-dimensional image is confirmed.

Advantageously, in step S3, the section image is obtained by manually or automatically selecting and marking mark points, in which a series of mark points are placed on a group of the original two-dimensional image or the reconstructed two-dimensional image and then connected through a smooth curve which represents an intersection position on the original two-dimensional image or the reconstructed two-dimensional image, between the section image and the original two-dimensional image, or between the section image and the reconstructed two-dimensional image.

Advantageously, when a position of the mark point is adjusted separately, the smooth curve will be automatically adjusted accordingly, so as to fit the mark point.

Advantageously, the three-dimensional ultrasound image display method further comprises marking a relative position of the section image or the reconstructed two-dimensional image on the original two-dimensional image.

Advantageously, the three-dimensional ultrasound image display method further comprises marking a relative position of the original two-dimensional image on the section image or the reconstructed two-dimensional image.

Advantageously, the step S5 further comprises when the feature point is indicated or moved on one section image, indicating or moving the feature point on corresponding positions of other section image, the original two-dimensional image or the reconstructed two-dimensional image in real time.

Advantageously, the feature point can be marked on the section image as the mark point.

Advantageously, the step S5 further comprises on any of the section image, the original two-dimensional image or the reconstructed two-dimensional image, when one specific feature pointed is selected, newly selecting all displayed original two-dimensional images, section images or reconstructed two-dimensional images to include the specific feature point.

Advantageously, the section image is a plane or a three-dimensional curved surface.

Advantageously, the means of image processing in step S3 comprises a projection or averaging algorithm.

Advantageously, in step S3, the reconstructed two-dimensional image represents ultrasonic echo signal strength by a brightness of each pixel which represents a relative or absolute depth of the ultrasonic echo in human tissue.

Advantageously, the section image or the reconstructed two-dimensional image further displays rotation information of the original two-dimensional image or the feature line or the feature surface.

The present application provides a three-dimensional ultrasound image display method, in which the original two-dimensional image is displayed in the three-dimensional space on the one hand, and one or more section images are displayed on the other hand, during the three-dimensional volumetric image display. Using this method, not only each section image can be displayed, but also the original two-dimensional image and its spatial position and direction can be displayed without any loss of image information. When selecting the feature points, the feature lines and the feature planes, the information of the original two-dimensional image is used, and meanwhile the information of the section image is also used to get a more accurate determination. This new method provides a more efficient and high-precision three-dimensional volumetric image display method which can be widely used in ultrasound and other three-dimensional imaging methods, including any system that needs to obtain image and spatial information on one surface at first and then implements a three-dimensional imaging process. As no X-ray is required, the present application makes it possible to carry out an on-site screening and large-scale screening for children, and provides a long-term monitoring way for the spine treatment.

DETAILED DESCRIPTION OF THE PREFERRED EMBODIMENT

To make the objective, the technical solution, and the advantage of the present application more clearly, the present application is further described in detail below with reference to the accompanying drawings and embodiments. It should be understood that the specific embodiments described herein are merely used to explain the present application and are not intended to the present application.

Figure 1:
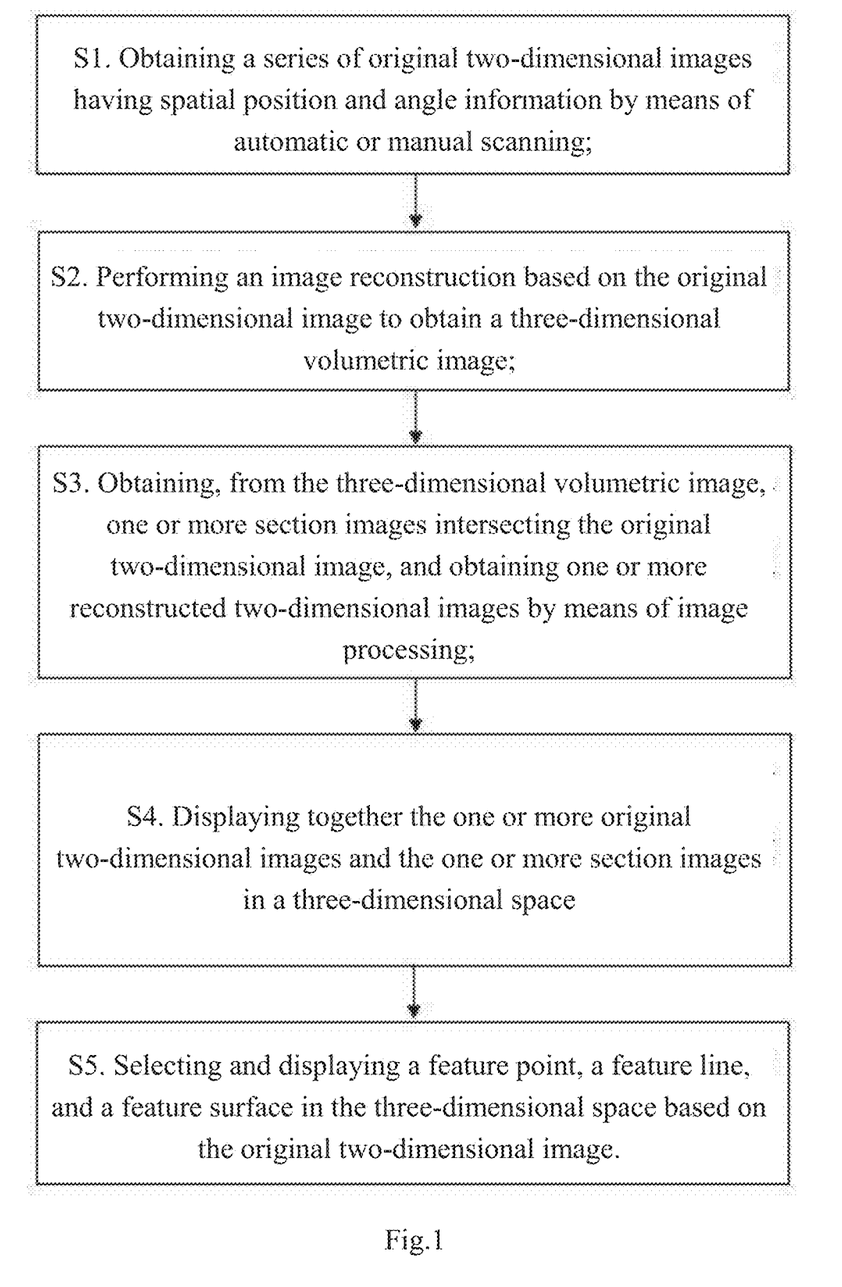
FIG. 1 is a flowchart of the method according to a preferable embodiment of the present application.

The present application can provide a three-dimensional ultrasound image display for the ultrasound scanning of various organs. In the present embodiment, the spine is taken as an example for explaining the three-dimensional ultrasound image display method of the present application in detail. As shown in FIG. 1, which is a flow chart of the three-dimensional ultrasound image display method according to the present application, it comprises following steps.

In step S1, a series of original two-dimensional images having spatial position and angle information are obtained by means of automatic or manual scanning.

In step S2, an image reconstruction is performed based on the original two-dimensional image to obtain a three-dimensional volumetric image.

In step S3, one or more section images intersecting the original two-dimensional image are obtained, and then one or more reconstructed two-dimensional images are obtained by means of image processing.

In step S4, the one or more original two-dimensional images and the one or more section images are displayed together in a three-dimensional space.

In step S5, a feature point, a feature line, and a feature surface are selected and displayed in the three-dimensional space based on the original two-dimensional image.

The original two-dimensional image in step S1 refers to a series of two-dimensional ultrasound images with spatial position and angle information obtained when the spine is scanned manually or mechanically by using the three-dimensional ultrasound imaging system. The original two-dimensional image is not smoothed or otherwise processed, and no image information is lost. The spine three-dimensional ultrasound imaging system has been disclosed in other patents, and will not be described here.

The three-dimensional volumetric image in step S2 is obtained by manners of image reconstruction based on the spatial position and angle information of the original two-dimensional image. In the reconstruction process, some parts that are not recorded by the original two-dimensional image are compensated by the interpolation algorithm, so as to get a complete three-dimensional volumetric image.

The three-dimensional volumetric image contains a number of section images in step S3. The image quality of the section image is not as good as the original two-dimensional image, and some original information may be lost.

The original two-dimensional image or section image can obtain the edge of spine structure through the edge detection, thus obtaining the three-dimensional volumetric image of the spine.

After scanning the spine with ultrasound, the projection of a certain surface can be displayed in a three-dimensional manner. As every pixel in the projection image is obtained by a voxel projection in a specific position in the three-dimensional space, the position of each pixel in the three-dimensional space is known. Voxel refers to the pixel in the three-dimensional space.

The section image in step S3 refer to the image obtained in the three-dimensional volumetric image and intersected the original two-dimensional image. This section image can be a plane, a simple curved surface (which can be stretched in one direction to form a plane), or a three-dimensional curved surface. The two-dimensional image reconstruction in step S3 is obtained by a comprehensive process of the original two-dimensional image information in a certain area, that is, the reconstruction of two-dimensional image is obtained by projecting the section image on a selected plane.

In step S3, the reconstructed two-dimensional image represents ultrasonic echo signal strength by a brightness of each pixel, however the brightness of each pixel represents a relative or absolute depth of the ultrasonic echo in human tissue. Hereby, the absolute depth means the depth counting from body surface, while the relative depth means the depth taking any position as the reference position, such as the position of the bone in the body, and so on.

Figure 2:
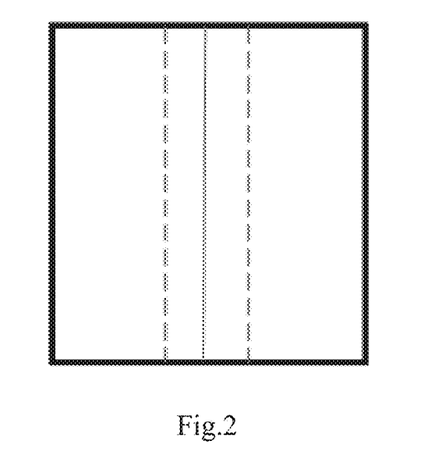
FIG. 2 is a schematic diagram showing the intersection position on the original two-dimensional image, between the section image and the original two-dimensional image, of the method according to a preferable embodiment of the present application.
Figure 3:
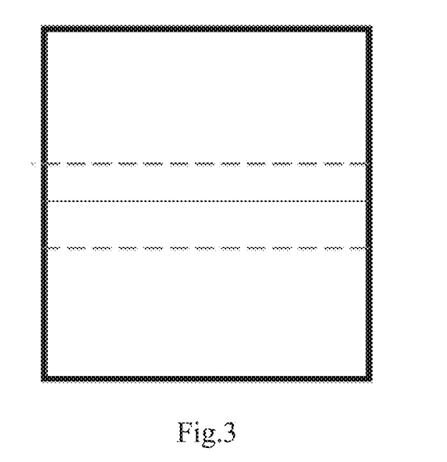
FIG. 3 is a schematic diagram showing the intersection position on the original two-dimensional image, between the section image and the original two-dimensional image at another angle, of the method according to a preferable embodiment of the present application.
Figure 4:
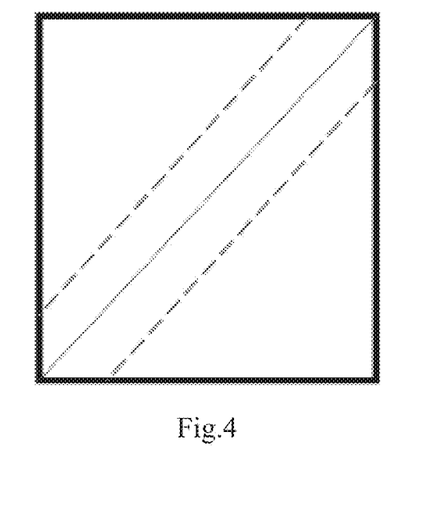
FIG. 4 is a schematic diagram showing the intersection position on the original two-dimensional image, between the section image and the original two-dimensional image at another angle, of the method according to a preferable embodiment of the present application.

The image processing in step S3 includes the maximum photometric projection method, i.e. selecting the pixel with the maximum photometric intensity in a certain area; the average projection method, i.e. averaging all pixels in a certain area; and the transparent projection method, i.e. setting the transparency according to the photometric value of the pixel. The above area can be marked on different original two-dimensional images. As shown in FIG. 2, FIG. 3 and FIG. 4, on the original two-dimensional image, a solid line is used to mark the intersection position of the reconstructed two-dimensional image and the original two-dimensional image, and the dotted lines on both sides of the solid line are used to mark the area range of information needed for the reconstruction of the reconstructed two-dimensional image.

The relative position of the section image or the reconstructed two-dimensional image also can be marked on the original two-dimensional image. Please continue to refer to FIG. 2, FIG. 3 and FIG. 4, if the square in the figure represents the original two-dimensional image, the solid line in the figure indicates the intersection position between the section image or reconstruction two-dimensional image and the original two-dimensional image. As shown in FIG. 2 or FIG. 3, the intersection position on the original two-dimensional image which intersects the section image or the reconstruction two-dimensional image is parallel to two opposite edges of the original two-dimensional image. As shown in FIG. 4, the intersection position between the section image or the reconstruction two-dimensional image and the original two-dimensional image may not be parallel to two opposite edges of the original two-dimensional image, but be incline to a certain angle, that is, the intersection position between the section image or the reconstruction two-dimensional image and the original two-dimensional image forms an angle greater than 0° and less than 90° with the two opposite edges of the original two-dimensional image.

Similarly, the relative position of the original two-dimensional image can also be marked on the section image or the reconstructed two-dimensional image.

Due to the inclined angle between the detection wave and the detected spine, the three lines in FIG. 2, FIG. 3 and FIG. 4 are separated. If the detection ultrasound beam and the detected spine are completely orthogonal, the above three lines will be combined into one line.

Figure 5:
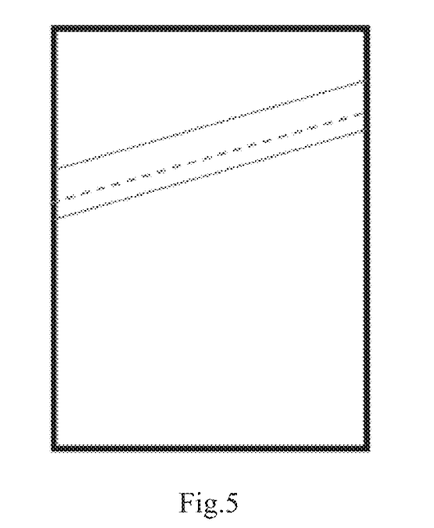
FIG. 5 is a schematic diagram showing the intersection position on the section image, between the section image and the original two-dimensional image, of the method according to a preferable embodiment of the present application.

The relative position of the original two-dimensional image can also be marked on the section image. As shown in FIG. 5, if the square in the figure represents the section image, and the dotted line indicates the intersection position where the section image intersects the original two-dimensional image, then the two solid lines in the figure indicate the relative position of the two opposite edges of the original two-dimensional image.

The section image can be orthogonal to the original two-dimensional image, or not, that is, the angle formed between the section image and the original two-dimensional image is greater than 0° and less than 90°.

Figure 6:
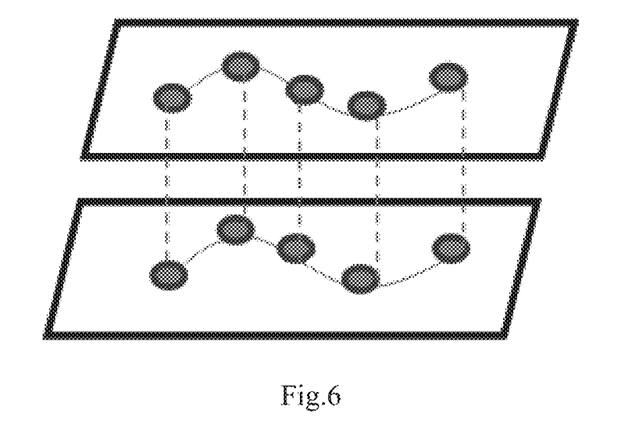
FIG. 6 is a schematic diagram of the method according to a preferable embodiment of the present application, in which the section image is a uniform simple curved surface having the same upside and downside.
Figure 7:
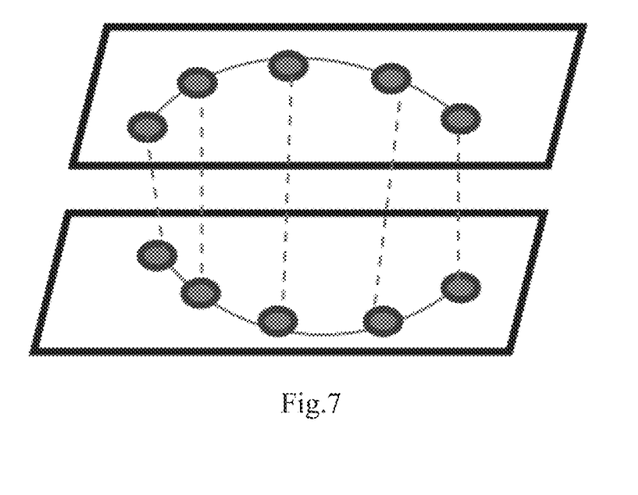
FIG. 7 is a schematic diagram of the method according to a preferable embodiment of the present application, in which the section image is a three-dimensional shape having different upside and downside.

The section image can be a plane or a curved surface. When the section image is a curved surface, it can be a simple curved surface having the same upside and downside as shown in FIG. 6, or a three-dimensional shape having different upside and downside as shown in FIG. 7. The two diamonds in FIG. 6 and FIG. 7 represent a plane parallel to the original two-dimensional image.

The angle formed by the intersection position between the section image and the original two-dimensional image or the reconstructed two-dimensional image, and the two opposite edges of the original two-dimensional image or the reconstructed two-dimensional image, whether the section image is orthogonal to the original two-dimensional image or the reconstructed two-dimensional image or not, and whether the section image is a plane or a curved surface, all depending on the acquisition of the section image.

Figure 8:
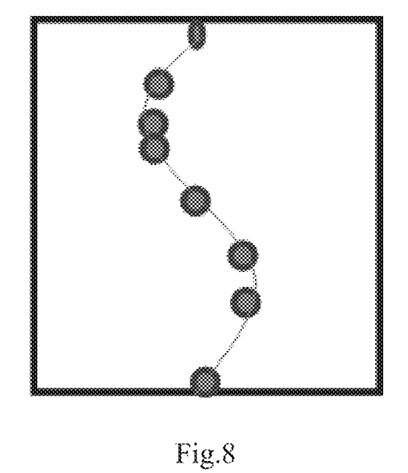
FIG. 8 is a schematic diagram showing the obtaining process of the section image formed by the selected points in the method according to a preferable embodiment of the present application.
Figure 9:
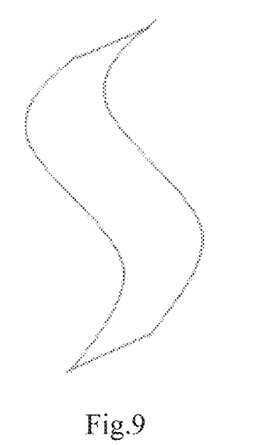
FIG. 9 is a schematic diagram showing the obtained section image formed by the selected points of FIG. 8.

As shown in FIG. 8 and FIG. 9, the acquisition of the section image described in step S3 is performed by manually or automatically selecting and marking the marking points. Specifically, a series of mark points are placed on a group of the original two-dimensional image or the reconstructed two-dimensional image and then connected through a smooth curve which represents an intersection position on the original two-dimensional image or the reconstructed two-dimensional image, between the section image and the original two-dimensional image or the reconstructed two-dimensional image. In addition, the plane where the section image locates is orthogonal to the plane where the original two-dimensional image and the reconstructed two-dimensional image locate. In relation to the original two-dimensional image or the reconstructed two-dimensional image, a section image of a curved surface is obtained in the orthogonal plane of the original two-dimensional image or reconstructed two-dimensional image, as shown in FIG. 8 and FIG. 9. Referring FIG. 8, the plane where the original two-dimensional image and the reconstructed two-dimensional image locate is parallel to the plane of FIG. 8, and the plane of the section image where the section image locates is orthogonal to the plane of FIG. 8.

Herein automatic means that a series of marker points can be automatically selected by the software according to the features in the image. For example, the needed mark points can be automatically identified according to the surface of the human body, the direction of the bone, the shape of the spine, the feature points of the spine bone in the image etc. For example, in the first reconstructed two-dimensional image in FIG. 14, the black part in the center of the image can be detected automatically from top to bottom, and the body surface information on the right side of the image in the second reconstructed two-dimensional image can be used for the automatic detection.

Figure 10:
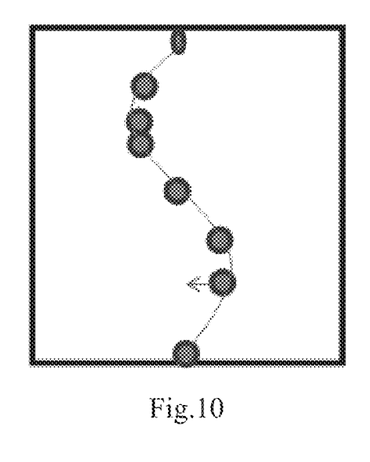
FIG. 10 is a schematic diagram showing the position of the smooth curve before the adjustment of the mark point in the method according to a preferable embodiment of the present application.
Figure 11:
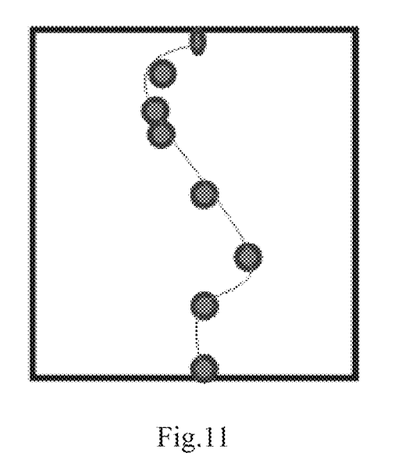
FIG. 11 is a schematic diagram showing the position of the smooth curve after the adjustment of the mark point in the method according to a preferable embodiment of the present application.
Figure 12:
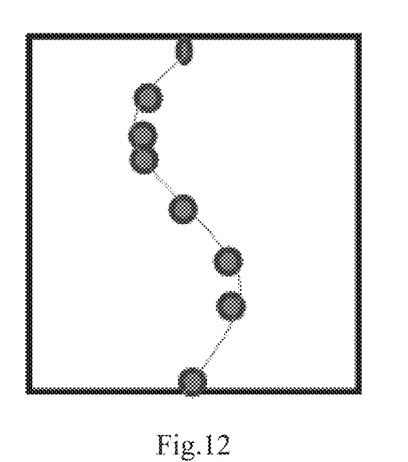
FIG. 12 is a schematic diagram showing the position of the smooth curve before its movement in the method according to a preferable embodiment of the present application.
Figure 13:
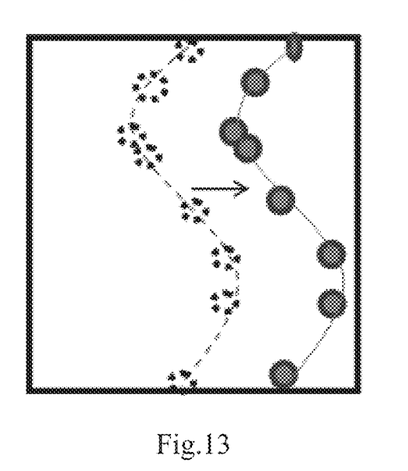
FIG. 13 is a schematic diagram showing the position of the smooth curve after its movement in the method according to a preferable embodiment of the present application.

The mark points selected above can be adjusted separately, and the smooth curve will be adjusted automatically according to the adjustment of the mark points, so as to fit the mark points, as shown in FIG. 10 and FIG. 11. The entire smooth curve can also be moved under the control of the mouse, as shown in FIG. 12 and FIG. 13.

In step S3, an image enhancement or pseudo color rendering is implemented on the original two-dimensional image, reconstructed two-dimensional image and section image for enhancing details displayed in the original two-dimensional image and the reconstructed two-dimensional image.

Figure 15:
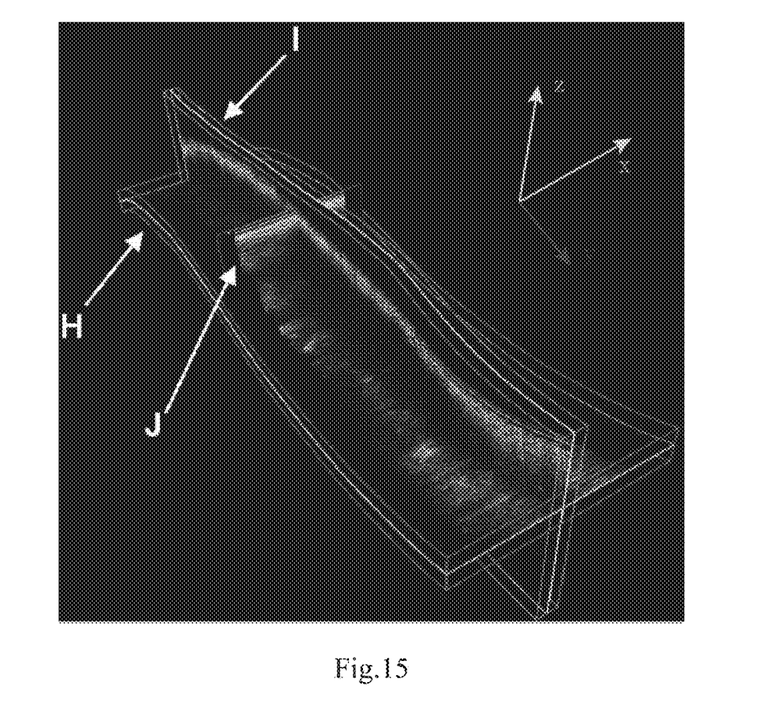
FIG. 15 is a schematic diagram showing the original two-dimensional image, the first section image and the second section image together in the three-dimensional space according to a preferable embodiment of the present application.

In step S4, the one or more original two-dimensional images and the one or more section images are displayed in a three-dimensional space together. As shown in FIG. 15, the original two-dimensional images and two section images are displayed in the three-dimensional space together.

In step S5, the step of selecting and displaying a feature point, a feature line, and a feature surface further comprises following steps:

S5-1. marking information of the feature point, the feature line or the feature surface on one of the original two-dimensional image, the section image or the reconstructed two-dimensional image;

S5-2. automatically displaying the information of the feature point, the feature line or the feature surface determined in S5-1 on the original two-dimensional image, the section image or the reconstructed two-dimensional image;

S5-3. determining whether the information of the feature point, the feature line or the feature surface marked in the original two-dimensional image, the section image or the reconstructed two-dimensional image is accurate or not;

S5-4. adjusting inaccurate marked information determined in S5-3 accordingly;

S5-5. repeating steps S5-2 to S5-4 until the information of the feature point, the feature line or the feature surface marked in the original two-dimensional image, the section image or the reconstructed two-dimensional image is confirmed.

In three-dimensional image science, the feature points refer to the key three-dimensional coordinate points with certain geometric significance, which are used to represent the local neighborhood relations and characteristics in the three-dimensional model. Feature point matrix can be used to store or represent the geometric contour, physiological characteristics and other attribute information of three-dimensional model. For example, features of the spine include the vertices of the edges, spinous process and transverse process.

The acquisition of the feature point, feature line and feature surface is to mark the required data position manually, semi automatically or automatically in the two-dimensional image or three-dimensional stereo image.

In the present embodiment, the step S5 further comprises when the feature point is indicated or moved on one section image, indicating or moving the feature point on corresponding positions of other section image, the original two-dimensional image or the reconstructed two-dimensional image in real time.

When the above feature points are marked, for example, when the left mouse button is clicked, the feature point will become a mark point, and the mark point will be marked on this image. Then the mouse can move to other images for operation, and the position of the mark point can be activated again by clicking the right mouse button, so that the feature point on this image can be moved again.

The step S5 further comprises on any of the section image, the original two-dimensional image or the reconstructed two-dimensional image, when one specific feature pointed is selected, newly selecting all displayed original two-dimensional images, section images or reconstructed two-dimensional images to include the specific feature point. After a specific position is selected, the existing spine model will adjust the model shape according to the specific position, so that the model can adapt to the detected spine.

For further explanation of this method, please refer to FIGS. 14-17, which are the schematic diagram of the certain original two-dimensional image, the schematic diagram of the original two-dimensional image displayed together with the first section image and the second section image in the three-dimensional space, the schematic diagram of the first reconstruction two-dimensional image and the schematic diagram of the second reconstruction two-dimensional image. Among them, the first reconstructed two-dimensional image is the projection of the first section image on one plane, and the second reconstructed two-dimensional image is the projection of the second section image on another plane.

Figure 14:
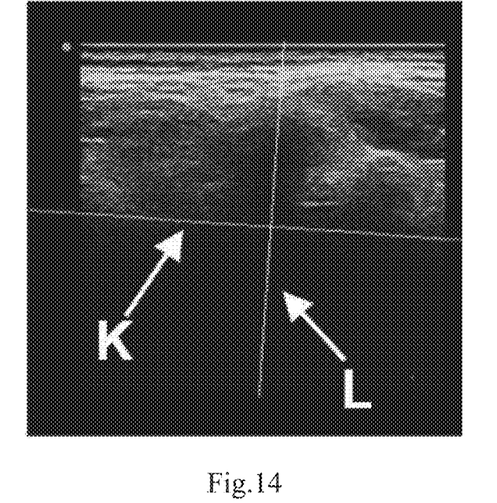
FIG. 14 is a schematic diagram of an original two-dimensional image according to a preferable embodiment of the present application.

FIG. 14 is a schematic diagram of certain original two-dimensional image. In FIG. 14, K is the boundary line between the first section image and the original two-dimensional image. There can be another two lines on both sides of the boundary line to mark the range of the first reconstructed two-dimensional image for projection processing. In FIG. 14, L is the boundary line between the second section image and the original two-dimensional image.

There can be another two lines on both sides to mark the range of the second reconstructed two-dimensional image for projection processing.

FIG. 15 is a schematic diagram showing the original two-dimensional image together with the first section image and the second section image in the three-dimensional space. In the Figure, H is the first section image, in which one line around the section image and located in the middle refers to the position of the first section image, and the other two lines are used to mark the range of the projection processing used to form the first reconstructed two-dimensional image. In the Figure, I is the second section image, in which one line around the section image and located in the middle refers to the position of the second section image, and the other two lines are used to mark the range of the projection processing used to form the second reconstructed two-dimensional image. In the Figure, J is the original two-dimensional image shown in FIG. 14.

Figure 16:
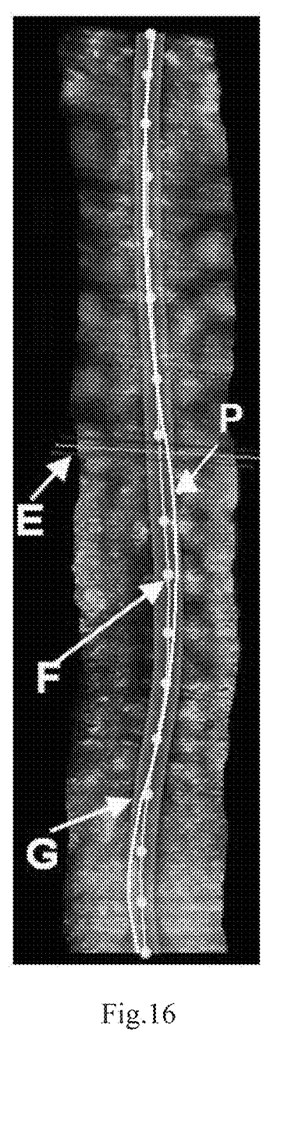
FIG. 16 is a schematic diagram of a first reconstructed two-dimensional image according to a preferable embodiment of the present application.

FIG. 16 is the schematic diagram of the first reconstructed two-dimensional image. The first reconstructed two-dimensional image is specifically the projection of the first section image on the xy plane in FIG. 15. E in the figure is a position mark on the first reconstructed two-dimensional image with respect to the original two-dimensional image shown in FIG. 14. The middle line refers to the boundary line between the original two-dimensional image and the first reconstructed two-dimensional image, and the two adjacent lines refer to the projection of two edges of the original two-dimensional image on the first reconstructed two-dimensional image. F in the figure refers to a series of mark points and their fitted curve on the first reconstructed two-dimensional image, which fitted curve determines the second section image, and then determines the second reconstructed two-dimensional image shown in FIG. 17. The mark of G on the first reconstructed two-dimensional image is corresponding to one area of the fitted curve in the original two-dimensional image shown in FIG. 14, which area determines the range of projection processing such as the maximum pixel value projection or the pixel average value of the second reconstructed two-dimensional image. The section image or the reconstructed two-dimensional image further displays the rotation information of the original two-dimensional image or the feature line or the feature plane. Specifically, P is a curve of the mark on the first reconstructed two-dimensional image relative to F, wherein the position of the curve deviating from F indicates the axial rotation amount of the original two-dimensional image or the obtained feature line and feature surface, while one or the other edge deviating from F indicates the rotation direction. The same method can be applied in FIG. 17.

Figure 17:
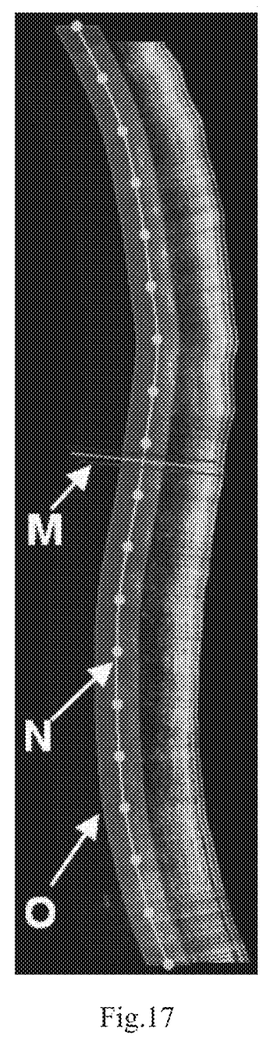
FIG. 17 is a schematic diagram of a second reconstructed two-dimensional image according to a preferable embodiment of the present application.

FIG. 17 is a schematic diagram of the second reconstructed two-dimensional image which is specifically the projection of the second section image on the yz plane in FIG. 15. In the figure, M is the position mark related to the original two-dimensional image on the second reconstructed two-dimensional image. The middle line refers to the boundary line between the original two-dimensional image and the second reconstructed two-dimensional image, and the two adjacent lines refer to the projection of two edges of the original two-dimensional image on the second reconstructed two-dimensional image. N in the figure refers to a series of mark points and their fitted curve on the second reconstructed two-dimensional image, which fitted curve determines the first section image, and then determines the first reconstructed two-dimensional image. The mark of O on the second reconstructed two-dimensional image is corresponding to one area of the fitted curve in the original two-dimensional image shown in FIG. 14, which area determines the range of projection processing such as the maximum pixel value projection or the pixel average value of the first reconstructed two-dimensional image.

Although the method of the present application is described with scoliosis as an example, however the present application is not limited to the application in scoliosis inspection, but also can be widely used in other three-dimensional ultrasound imaging methods, including any system that needs to obtain image and spatial information on one surface at first and then implements a three-dimensional imaging process.

As no X-ray is required, the present application makes it possible to carry out an on-site screening and large-scale screening for children, and provides a long-term monitoring way for the spine treatment. Since this method does not require harmful radiation to operate, it can be used in any patient without limiting the time or frequency. It is possible to evaluate scoliosis monthly, weekly or daily. In the treatment of scoliosis, continuous monitoring results are very important. On the opposite, the standard X-ray assessment limits the time between successive assessments to three to nine months, due to the radiation hazards.

The foregoing is a further detailed description of the present application in connection with specific preferred embodiments, and cannot be considered as that the specific implementation of the present application is limited to these illustrations. It will be apparent to those skilled in the art that any various modifications or substitutions may be made to the present application without departing from the spirit of the invention, and such modifications or substitutions should be considered as falling within the scope of the present application.

The invention claimed is:

1. A three-dimensional ultrasound image display method comprising following steps:
   S1. obtaining a series of original two-dimensional images having spatial position and angle information by means of automatic or manual scanning;
   S2. performing an image reconstruction based on the original two-dimensional image to obtain a three-dimensional volumetric image;
   S3. obtaining, from the three-dimensional volumetric image, one or more section images intersecting the original two-dimensional image, and obtaining one or more reconstructed two-dimensional images by means of image processing;
   S4. displaying together the one or more original two-dimensional images and the one or more section images in a three-dimensional space; and
   S5. selecting and displaying a feature point, a feature line, and a feature surface in the three-dimensional space based on the original two-dimensional image;
   wherein in step S5, a step of selecting and displaying a feature point, a feature line, and a feature surface further comprises following steps:
   S5-1. marking information of the feature point, the feature line or the feature surface on one of the original two-dimensional image, the section image or the reconstructed two-dimensional image;
   S5-2. automatically displaying the information of the feature point, the feature line or the feature surface determined in S5-1 on the original two-dimensional image, the section image or the reconstructed two-dimensional image;
   S5-3. determining whether the information of the feature point, the feature line or the feature surface marked in the original two-dimensional image, the section image or the reconstructed two-dimensional image is accurate or not;

S5-4. adjusting inaccurate marked information determined in S5-3 accordingly;

S5-5. repeating steps S5-2 to S5-4 until the information of the feature point, the feature line or the feature surface marked in the original two-dimensional image, the section image or the reconstructed two-dimensional image is confirmed.

2. The three-dimensional ultrasound image display method according to claim 1, wherein further comprising implementing an image enhancement or pseudo color rendering on the original two-dimensional image, reconstructed two-dimensional image and section image for enhancing details displayed in the original two-dimensional image and the reconstructed two-dimensional image.

3. The three-dimensional ultrasound image display method according to claim 1, wherein in step S3, the section image is obtained by manually or automatically selecting and marking mark points, in which a series of mark points are placed on a group of the original two-dimensional image or the reconstructed two-dimensional image and then connected through a smooth curve which represents an intersection position on the original two-dimensional image or the reconstructed two-dimensional image, between the section image and the original two-dimensional image, or between the section image and the reconstructed two-dimensional image.

4. The three-dimensional ultrasound image display method according to claim 3, wherein when a position of the mark point is adjusted separately, the smooth curve will be automatically adjusted accordingly, so as to fit the mark point.

5. The three-dimensional ultrasound image display method according to claim 1, wherein further comprising marking a relative position of the section image or the reconstructed two-dimensional image on the original two-dimensional image.

6. The three-dimensional ultrasound image display method according to claim 1, wherein further comprising marking a relative position of the original two-dimensional image on the section image or the reconstructed two-dimensional image.

7. The three-dimensional ultrasound image display method according to claim 1, wherein the step S5 further comprises when the feature point is indicated or moved on one section image, indicating or moving the feature point on corresponding positions of other section image, the original two-dimensional image or the reconstructed two-dimensional image in real time.

8. The three-dimensional ultrasound image display method according to claim 7, wherein the feature point can be marked on the section image as the mark point.

9. The three-dimensional ultrasound image display method according to claim 1, wherein the step S5 further comprises on any of the section image, the original two-dimensional image or the reconstructed two-dimensional image, when one specific feature pointed is selected, newly selecting all displayed original two-dimensional images, section images or reconstructed two-dimensional images to include the specific feature point.

10. The three-dimensional ultrasound image display method according to claim 1, wherein the section image is a plane or a three-dimensional curved surface.

11. The three-dimensional ultrasound image display method according to claim 1, wherein the means of image processing in step S3 comprises a projection or averaging algorithm.

12. The three-dimensional ultrasound image display method according to claim 1, wherein in step S3, the reconstructed two-dimensional image represents ultrasonic echo signal strength by a brightness of each pixel which represents a relative or absolute depth of the ultrasonic echo in human tissue.

13. The three-dimensional ultrasound image display method according to claim 1, wherein the section image or the reconstructed two-dimensional image further displays rotation information of the original two-dimensional image or the feature line or the feature surface.

* * * * *